(12) United States Patent
Langley et al.

(10) Patent No.: US 7,008,405 B2
(45) Date of Patent: Mar. 7, 2006

(54) DRIVE MECHANISM FOR AN INJECTION DEVICE

(75) Inventors: Christopher Nigel Langley, Leamington Spa (GB); Robert Woolston, Moreton Morrell (GB)

(73) Assignee: DCA Design International Limited, Warwick (GB)

( * ) Notice: Subject to any disclaimer, the term of this patent is extended or adjusted under 35 U.S.C. 154(b) by 310 days.

(21) Appl. No.: 10/471,717

(22) PCT Filed: Mar. 26, 2002

(86) PCT No.: PCT/GB02/01435

§ 371 (c)(1),
(2), (4) Date: Sep. 15, 2003

(87) PCT Pub. No.: WO02/076531

PCT Pub. Date: Oct. 3, 2002

(65) Prior Publication Data

US 2004/0092876 A1    May 13, 2004

(51) Int. Cl.
*A61M 5/00*    (2006.01)
*A61M 5/315*    (2006.01)

(52) U.S. Cl. .................... 604/211; 604/218; 604/232

(58) Field of Classification Search ................ 604/211
See application file for complete search history.

(56) References Cited

U.S. PATENT DOCUMENTS

| 4,659,327 A * | 4/1987 | Bennett et al. .............. 604/135 |
| 5,032,117 A | 7/1991 | Motta |
| 5,858,000 A | 1/1999 | Novacek et al. |
| 5,957,896 A | 9/1999 | Bendek et al. |
| 6,004,297 A | 12/1999 | Steenfeldt-Jensen et al. |
| 6,613,019 B1 * | 9/2003 | Munk ........................ 604/187 |
| 2002/0107487 A1 * | 8/2002 | Preuthun .................... 604/218 |

FOREIGN PATENT DOCUMENTS

WO    WO 94/03222    2/1994

* cited by examiner

*Primary Examiner*—Michael J. Hayes
(74) *Attorney, Agent, or Firm*—Oliff & Berridge, PLC

(57) ABSTRACT

Injection devices are known for the self administration of medicament by patients. The medicament is typically contained within a cartridge located within the injection device. It is a problem that injection devices should be small enough to fit into a jacket pocket or a hand bag without difficulty. Also, the injection device must be of a size that enables a piston or similar used to drive the Cartridge bung within the cartridge to be moved both to a maximum dispense position within the cartridge and to be fully withdrawn from the cartridge to allow for replacement of the cartridge. A drive mechanism for an injecting device is disclosed in which the drive mechanism comprises a displaceable dosing spindle 6, a dial dose means 8, a transmission means 10, and a cable means 12, a piston comprising a plurality of nested piston members 30, 32, 34, displacement of the transmission means 10 causing the cable means 12 to move at least one of one of the nested piston members to drive a cartridge bung 18.

10 Claims, 4 Drawing Sheets

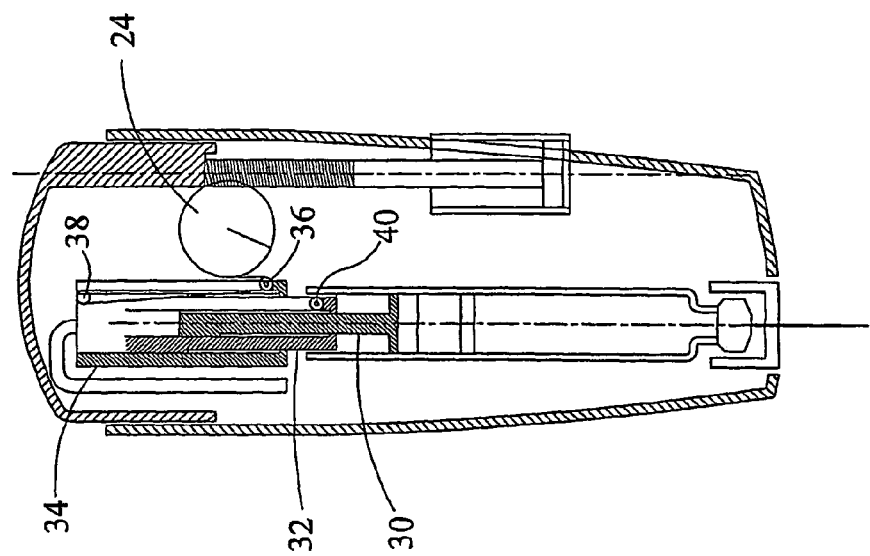
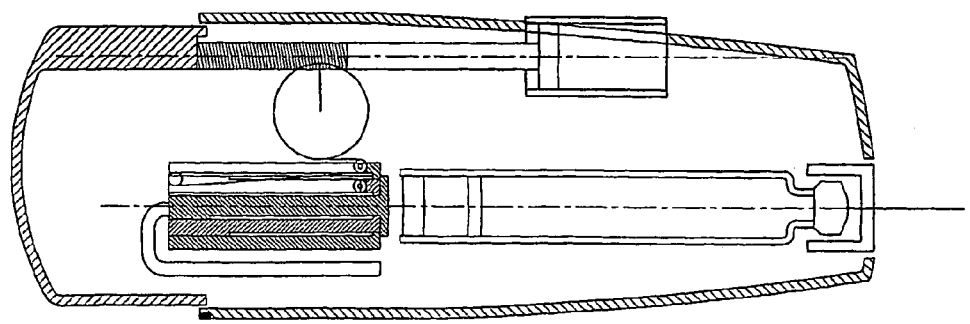

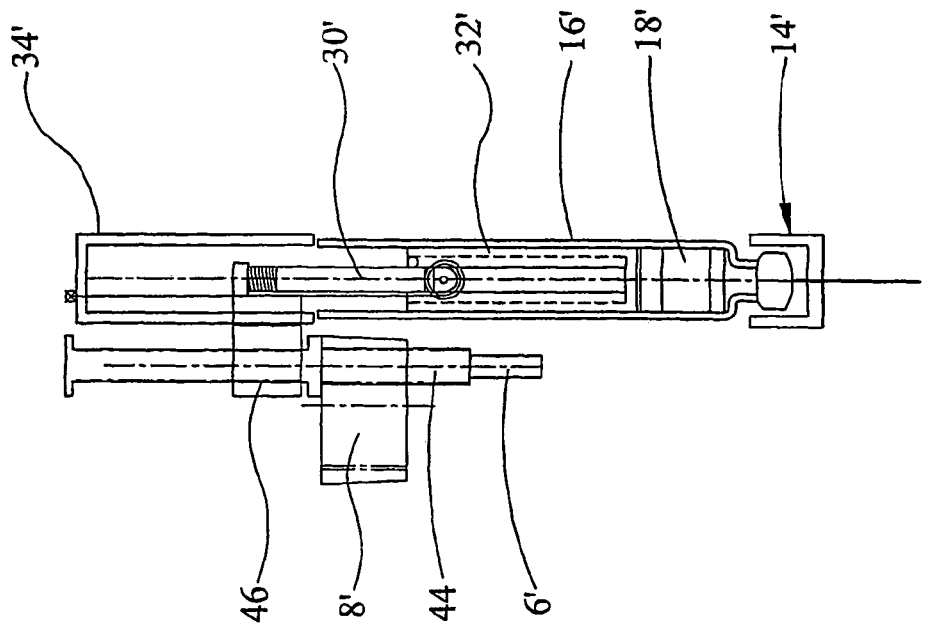
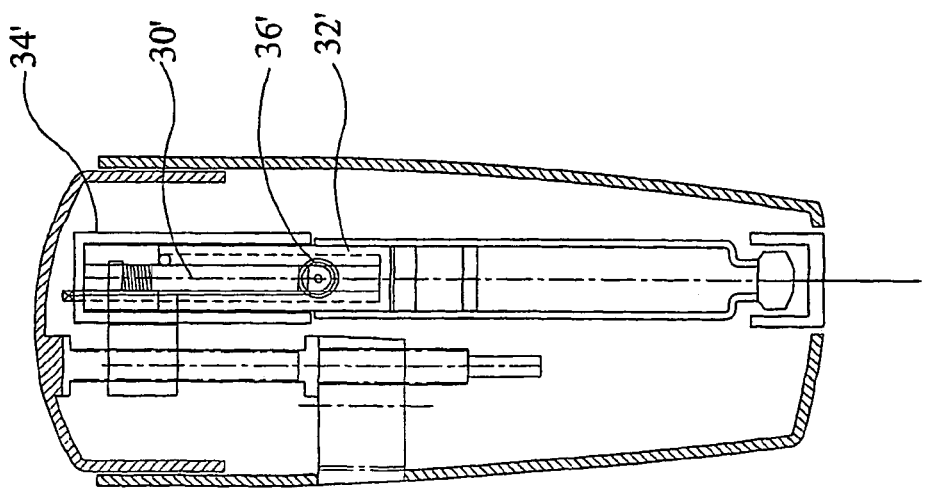

DRIVE MECHANISM FOR AN INJECTION DEVICE

The present invention relates to improvements in an injection device, and in particular to improvements to a drive mechanism for a portable injection device for dispensing controlled quantities of a medicament.

Injection devices are known for the self administration of medicament by patients. For example, those suffering from diabetes may require regular injections of insulin. Injection devices allow the patient to select a dose and to administer that dose. It is known to automate this process so that a user need only press a button and the injection device will dispense a selected dose of medicament. This relieves the patient of the task of controlling the amount dispensed while manually expelling the medicament from the injection device. This is a particular problem for the elderly, the in firm, those suffering from vision difficulties and others suffering from diabetes related problems which impair their faculties.

The medicament is typically contained within a cartridge located within the injection device. The cartridge has a bung or piston at one end which is driven towards a second end of the cartridge to expel the medicament from the injection device. It is a problem that injection devices should be small enough to fit into a jacket pocket or a hand bag without difficulty. At the same time, the injection device must be of a size that enables a piston or the like used to drive the cartridge bung within the cartridge to be moved both to a maximum dispense position within the cartridge and to be fully withdrawn from the cartridge to allow for replacement of the cartridge.

It is an advantage of the present invention that it seeks to provide a solution to these conflicting requirements.

According to a first aspect of the present invention, a drive mechanism for an injection device in which a piston is successively moved in relation to a first end of a medicament cartridge containing a medicament selectively to drive a bung closing a first end of the medicament cartridge into the medicament cartridge to expel medicament through a delivery member located at a second end of the medicament cartridge, is disclosed in which the drive mechanism further comprises a displaceable dosing spindle, a dial dose means, a transmission means, and a cable means, the piston comprising a plurality of nested piston members, displacement of the transmission means causing the cable means to move at least one of one of the nested piston members to drive the bung.

In a first embodiment, the cable is connected at a first end to the transmission means and at a seconded to one of the piston members. Preferably the transmission means comprises a spool onto which the cable means is wound, the spool being provided with teeth which engage a threaded portion provided on the displaceable dosing spindle. More preferably the second end of the cable means is connected to an inner piston member and that an intermediate part of the cable means between the first and second ends of the cable means runs over guide means located on other of the nested piston members.

Alternatively the cable may be connected at a first end to an outer piston member and at a second end to an intermediate piston member, the transmission means being adapted to precess along a threaded portion provided on the displaceable dosing spindle. Preferably the transmission means comprises a claw member connected to an inner piston member and that an intermediate part of the cable means between the first and second ends of the cable means runs over a guide means located on the inner piston member.

According to a second aspect of the present invention, an injection device incorporates a drive mechanism according to the first aspect of the invention.

Preferably, the injection device further comprises a displaceable button, displacement of the button causing displacement of the dosing spindle.

The invention will now be described, by way of example only, with reference to the accompanying drawings in which:

FIG. 4 shows a view similar to FIG. 3 after dialling of a required dosage;

FIG. 5 shows a view similar to FIG. 4 after delivery of the required dosage;

FIG. 9 shows a view similar to FIG. 8 after delivery of the required dosage; and FIG. 10 shows aside section of a mechanism for use with the injection device of FIGS. 6 to 9.

Like reference numerals will be used to refer to like parts of the injection device.

Figure 1:
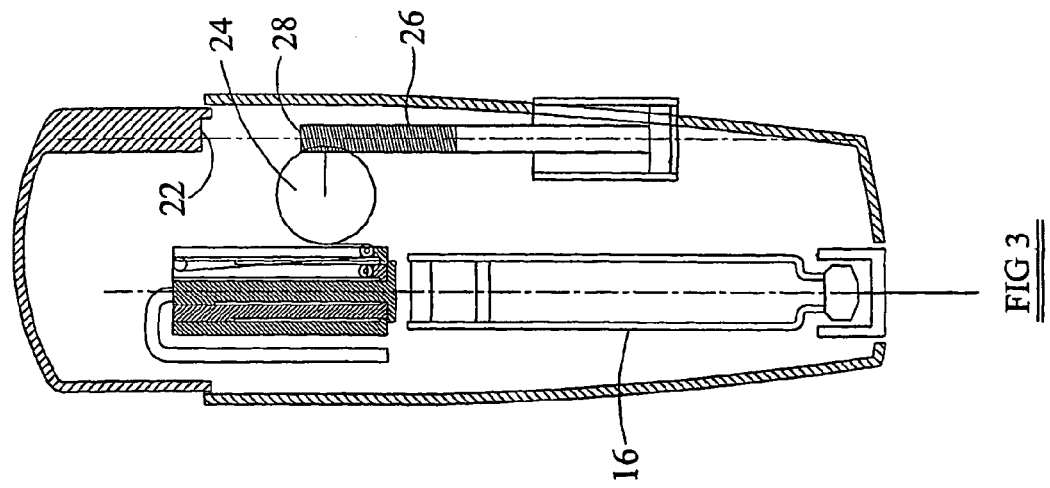
FIG. 1 shows inside section a first embodiment of an injection device having a delivery device according to the present invention.

Referring first to FIGS. 1 to 5, there maybe seen a portable injection device incorporating a drive mechanism in accordance with the first aspect of the present invention.

The injection device 2 comprises a main housing 4 in which the drive mechanism is located and a button 20. The dive mechanism comprises a displaceable dosing spindle 6, a dial dose means 8, a transmission means 10, a cable means 12 and a piston. A needle unit 14 including a delivery member in the form a hollow needle is secured to a first end of the main housing 4. A medicament cartridge 16 having a first end and a second end may be stored in the main housing 4. When the needle unit 14 is in place, the needle unit 14 pierces a flexible membrane at the first end of the medicament cartridge 16. A displaceable bung 18 is located at the second end of the medicament cartridge 16. A cover (not shown) maybe provided over the first end of the main housing 4 to protect the needle unit 14 from damage and a user from inadvertent pricking by the needle.

The button 20, as shown in the illustrated embodiment, is preferably in the form of a cap or cup adapted for slidable movement within the main housing 4 as shown in the illustrated embodiment. The main housing 4 and the button 20 are preferably provided with a catch (not shown) releasably to retain the button 20 in a closed or 'off' position. The button 20 is provided with a stop member 22 on an inner side of the button 20. In the illustrated embodiment, the stop member 22 is formed as a shoulder to one side of the button 20.

The dial dose means 8 is located to the side of the main housing 4. The dial dose means 8 is used by a user to select a dosage of medicament to be dispensed from the injection device 2 in a manner to be described.

The transmission means 10 comprises a spool 24 from which the cable means 12 can be deployed The spool 24 is provided with a plurality of teeth about a peripheral surface thereof.

The dosing spindle 6 is provided along at least a part of its length with a threaded portion 26. The teeth of the spool 24 engage with the threaded portion 26 of the dosing spindle 6. A first end of the dosing spindle 6 is connected to the dose dial means 8 such that dialling of a dose causes rotation of the dosing spindle 6. A second end of the dosing spindle 6 is provided with an abutment surface 28.

The piston comprises a plurality of nested piston members. In the illustrated embodiment, the piston comprises an outer piston member 34, an intermediate piston member 32 and an inner piston member 30. The outer piston member 34 is fixed in relation to the main housing 4. The intermediate piston member 32 is nested for relative movement with respect to and within the outer member 34. The inner piston member 30 is nested for relative movement with respect to and within the intermediate piston member 32. A first end of the inner piston member 30 extends beyond the intermediate piston member 32 and the outer piston member 34. The first end of the inner piston member 30 is adapted in use to selectively drive the bung 18 into the medicament cartridge 16 to expel medicament through the delivery member.

Figure 2:
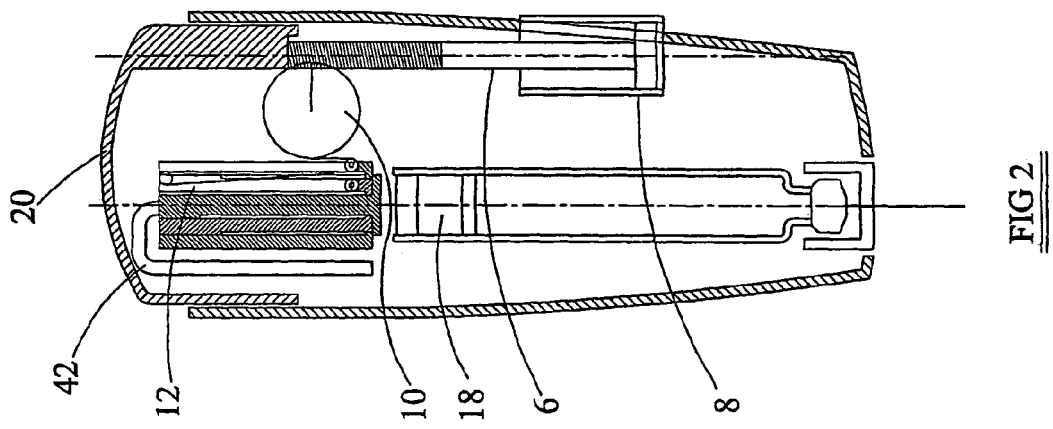
FIG. 2 shows a side section similar to FIG. 1 with a path of the cable means shown more clearly.

The intermediate piston member 32 and the outer piston member 34 are each provided with guide means about which the cable means 12 is adapted to run. The cable means 12 is secured at a first end to the spool 24 and at a second end to the inner piston member 30. In the illustrated embodiment, the cable means 12 runs from the spool 24 over a first guide means 36 provided on the outer piston member 34, over a second guide means 38 provided at a second end of the intermediate piston member 32, over a third guide means 40 provided at a first end of the intermediate piston member 32 to the inner piston member 30. In the illustrated embodiment, the cable means 12 is secured at a second end of the inner piston member 30 (FIG. 2)

A return means 42 is located between the second end of the inner piston member 30 and the main housing 4. The return means 42 may take any suitable form, for example spring means such as a helical spring.

Figure 3:
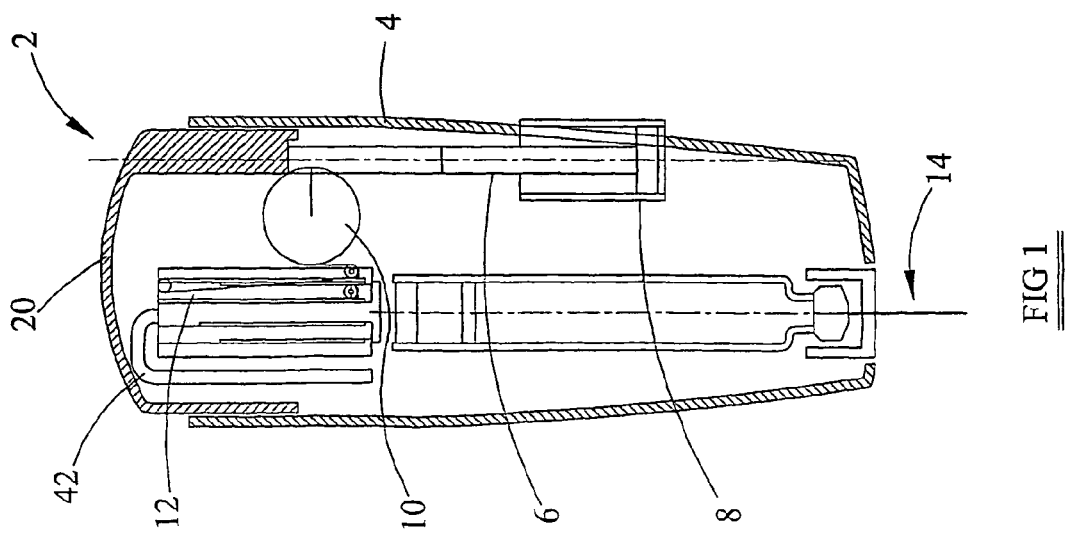
FIG. 3 shows a similar view to FIG. 2 with the injection device in a ready position.
Figure 8:
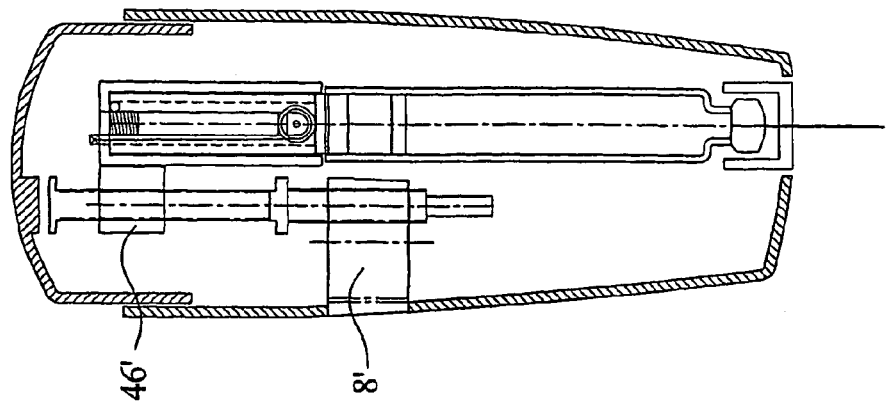
FIG. 8 shows a view similar to FIG. 7 after dialling of a required dosage.

In use, a user releases the button 20 to ready the injection device 2 (FIG. 3). A user then dials a required dose using the dial dose means 8. This causes the dosing spindle 6 to rotate and precess along its axis towards a second end of the housing 4. From FIG. 4, it can be seen that a dose has been dialled and that the abutment surface 28 at the second end of the dosing spindle 6 has been moved into contact with the stop member 22 on the inside of the button 20.

The button 20 may now be pressed to deliver the dialled dosage of medicament. As the button 20 is driven towards the first end of the housing 4, the stop member 22 on the button 20 pushes the abutment surface 28 of the dosing spindle 6 such that the dosing spindle 6 is also driven towards the fist end of the housing 4. Since the dosing spindle 6 is not rotated, the spool 24 is rotated to draw the cable means onto the spool, thereby shortening the effective length of the cable means between the spool and the inner piston member 30.

This causes the inner piston member 30 and the intermediate piston member 32 to be drawn out of the nested position and the inner piston member 30 to be advanced towards the medicament cartridge bung 18 to drive the medicament cartridge bung 18 forward to expel medicament from the medicament cartridge 16 (FIG. 5).

This process maybe repeated until the medicament cartridge 16 is empty, the medicament cartridge contains insufficient medicament to deliver the dialled dose or some other condition is met. The piston may then be withdrawn by allowing the dosing spindle 6 to rotate freely such that the inner piston member 30 can be drawn back to a nested position under the action of there turn means 42. In normal use, the dosing spindle 6 may only be rotated under the action of the dial dose means 8.

A second embodiment of the invention is shown in FIGS. 6 to 10. The injection device comprises a main housing 4' in which the drive mechanism is located and a button 20'. The drive mechanism comprises a displaceable dosing spindle 6', a dial dose means 8', a transmission means 10', a cable means 12' and a piston. A needle unit 14' including a delivery member in the form a hollow needle is secured to a first end of the main housing 4'. A medicament cartridge 16' having a first end and a second end may be stored in the main housing 4'. When the needle unit 14' is in place, the needle unit 14' pierces a flexible membrane at the first end of the medicament cartridge 16'. A displaceable bung 18' is located at the second end of the medicament cartridge 16'. A cover (not shown) ray be provided over the first end of the main housing 4' to protect the needle unit 14' from damage and a user from inadvertent pricking by the needle.

The button 20', as shown in the illustrated embodiment, is preferably in the form of a cup adapted for slidable movement within the main housing 4' as shown in the illustrated embodiment. The main housing 4' and the button 20' are preferably provided with a catch (not shown) releasably to retain the button 20' in a closed or off position. The button 20' is provided with a stop member 22' on an inner side of the button 20'. In the illustrated embodiment, the stop member 22' is formed as a extension formed on an inner surface of the button 20'.

The dial dose means 8' is located to one side of the main housing 4'. The dial dose means 8' is used by a user to select a dosage of medicament to be dispensed from the injection device 2' in a manner to be described.

The dosing spindle 6' comprises a radially extending flange about apportion intermediate between a first end of the dosing spindle 6' and a second end of the dosing spindle 6'. A spline 44 is provided about the first end of the dosing spindle 6' whereby the dosing spindle 6' is connected to the dial dose means 8' such that dialling of a dose causes rotation of the dosing spindle 6'. A second end of the dosing spindle 6' is provided with an abutment surface 28'. The second end of the dosing spindle 6' is provided with a threaded portion 26' along at least a part thereof.

The piston comprises a plurality of nested piston members. In the illustrated embodiment, the piston comprises an outer piston member 34', an intermediate piston member 32' and an inner piston member 30'. The outer piston member 34' is fixed in relation to the main housing 4' and receives the inner piston member 30' and the intermediate piston member 32' therein. The intermediate piston member 32' is nested for relative movement with respect to and within the outer piston member 34'. The inner piston member 30' is nested for relative movement with respect to and within the intermediate piston member 32'. A first end of the intermediate piston member 32' extends beyond the inner piston member 30' and the outer piston member 34'. The first end of the intermediate piston member 32' is adapted in use to selectively drive the bung 18' into the medicament cartridge 16' to expel medicament through the delivery member.

The inner piston member 30' is provided with guide means 36' about which the cable means 12' is adapted to run. The cable means 12' is secured at a first end to the outer piston member 34' and at a second end to the intermediate piston member 32'. In the illustrated embodiment, the cable means 12' runs from the outer piston member 34' over the guide means 36' provided on the inner piston member 30' to where the cable means 12' is secured to the intermediate piston member 32'.

The transmission means 10' comprises a claw 46. The claw 46 is mounted on the second end of the dosing spindle 6' such that the dosing spindle 6' may precess therethrough. The claw 46 is connected to a second end of the inner piston member 30'.

Figure 7:
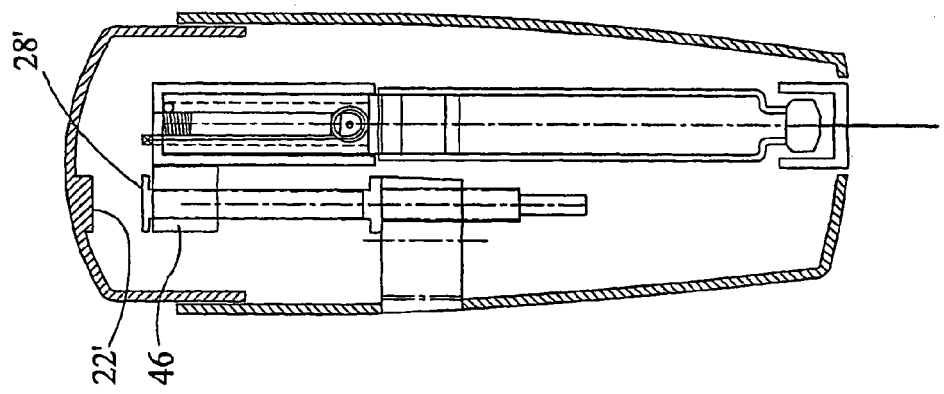
FIG. 7 shows a similar view to FIG. 6 with the injection device in a ready position.
Figure 6:
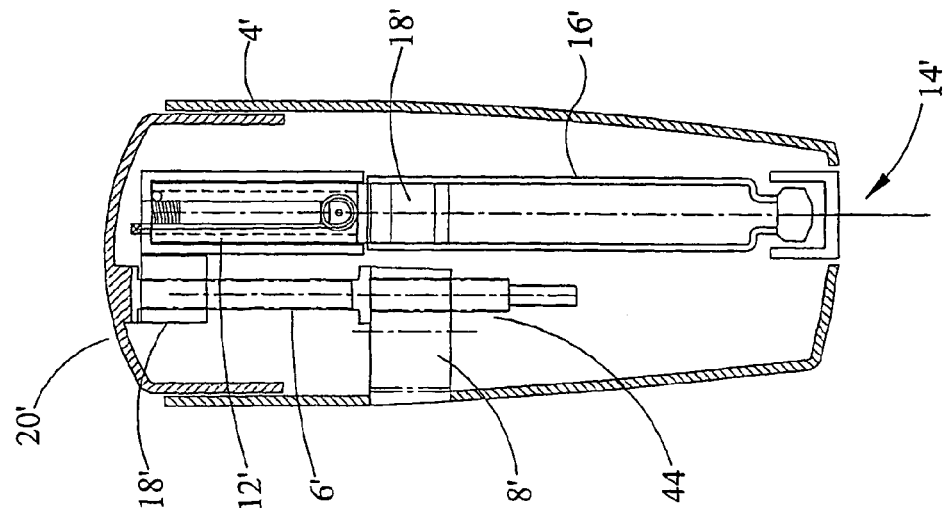
FIG. 6 shows in side section a second embodiment of an injection device having a delivery device according to the present invention.

In use, a user releases the button 20' to ready the injection device 2' (FIG. 7). A user then dials a required dose using the dial dose means 8'. This causes the dosing spindle 6' to rotate and precess along its axis through the claw 46 towards a second end of the housing 4'. From FIG. 8, it can be seen that a dose has been dialled and that the abutment surface 28' at the second end of the dosing spindle 6' has been moved towards the stop member 22' on the inside of the button 20'.

The button 20' may now be pressed to deliver the dialled dosage of medicament. As the button 20' is driven towards the first end of the housing 4', the stop member 22' on the button 20' meets the abutment surface 28' of the dosing spindle 6' such that the dosing spindle 6' is also driven towards the first end of the housing 4'. Since the dosing spindle 6' is not rotated, the claw 46 is moved towards the first end of the housing 4' together with the inner piston member 30' attached thereto. This pushes the inner piston member 30' away from the outer piston member 34'. This has the effect of causing the cable means 12' to draw the intermediate piston member 32' out of the outer piston member 34' and be advanced towards the medicament cartridge bung 18' to drive the medicament cartridge bung 18' forwards to expel medicament from the medicament cartridge 16' (FIG. 9).

This process maybe repeated until the cartridge 16' is empty, the medicament cartridge contains insufficient medicament to deliver the dialled dose or some other condition is met (FIG. 10).

The relative arrangement of the drive mechanism and the medicament cartridge means that the main housing provides a relatively large flat face where a relatively large dose display, such as a liquid crystal display may be located. This in turn enables the dose display to use relatively large figures or other characters. This is an advantage for those with impaired vision.

What is claimed is:

1. A drive mechanism for an injection device in which a piston, comprising a plurality of nested piston members, is successively moved in relation to a first end of a medicament cartridge containing a medicament selectively to drive a bung closing a first end of the medicament cartridge into the medicament cartridge to expel medicament through a delivery member located at a second end of the medicament cartridge and further comprising a dial dose means, is characterised in that the drive mechanism yet further comprises a displaceable dosing spindle, a cable means and a transmission means displaceable to cause the cable means to move at least one of the plurality of nested piston members to drive the bung.

2. A drive mechanism according to claim 1, characterised in that the cable is connected at a first end to the transmission means and at a second end to one of the piston members.

3. A dive mechanism according to claim 2, characterised in that the transmission means comprises a spool onto which the cable means is wound, the spool being provided with teeth which engage a threaded portion provided on the displaceable dosing spindle.

4. A drive mechanism according to claim 2, characterised in that return means are provided to return the nested piston members to a retracted position.

5. A drive mechanism according to claim 1, characterised in that the transmission means comprises a spool onto which the cable means is wound, the spool being provided with teeth which engage a threaded portion provided on the displaceable dosing spindle.

6. A drive mechanism according to claim 5 characterised in that the second end of the cable means is connected to an inner piston member and that an intermediate part of the cable means between the first and second ends of the cable means runs over guide means located on other of the nested piston members.

7. A drive mechanism according to claim 6, characterised in that return means are provided to return the nested piston members to a retracted position.

8. A drive mechanism according to claim 5, characterised in that return means are provided to return the nested piston members to a retraced position.

9. A drive mechanism according to claim 1, characterised in that return means are provided to return the nested piston members to a retracted position.

10. A drive mechanism according to claim 9, characterised in that return means comprises spring means.

* * * * *